US00PP37759P2

(12) United States Plant Patent
Mousa

(10) Patent No.: US PP37,759 P2
(45) Date of Patent: Oct. 13, 2026

(54) *KALANCHOE* PLANT NAMED 'Dokalvola'

(50) Latin Name: *Kalanchoe blossfeldiana*
Varietal Denomination: Dokalvola

(71) Applicant: DUMMEN GROUP B.V., De Lier (NL)

(72) Inventor: Rami Mousa, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/420,732

(22) Filed: Dec. 15, 2025

(51) Int. Cl.
*A01H 5/02* (2018.01)
*A01H 6/32* (2018.01)

(52) U.S. Cl.
USPC ..... Plt./338

(58) Field of Classification Search
USPC ..... Plt./338
See application file for complete search history.

(56) References Cited

U.S. PATENT DOCUMENTS

PP32,482 P2 * 11/2020 Vlielander ..... A01H 6/324
Plt./336

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Kalanchoe* plant named 'Dokalvola', characterized by its compact, upright and uniformly mounded plant habit; moderately vigorous growth habit and rapid growth rate; freely branching plant habit; dark green-colored leaves; uniform, early and freely flowering habit; large single-type flowers that are vivid reddish orange in color; excellent postproduction longevity; and relative tolerance to high temperatures.

1 Drawing Sheet

Botanical designation: *Kalanchoe blossfeldiana.*
Cultivar denomination: 'DOKALVOLA'.

BACKGROUND OF THE INVENTION

The present invention relates to a new and distinct *Kalanchoe* plant, botanically known as *Kalanchoe blossfeldiana* and hereinafter referred to by the name 'Dokalvola'.

The new *Kalanchoe* is a product of a planned breeding program conducted by the Inventor in De Lier, The Netherlands. The objective of the breeding program is to create new freely-branching and freely-flowering *Kalanchoe* plants with large single-type yellow-colored flowers.

The new *Kalanchoe* plant originated from a cross-pollination made by the Inventor in De Lier, The Netherlands in 2016 of a proprietary selection of *Kalanchoe blossfeldiana* identified as code number KA15-000584-001, not patented, as the female, or seed, parent with a proprietary selection of *Kalanchoe blossfeldiana* identified as code number KA15-000623-001, not patented, as the male, or pollen, parent. The new *Kalanchoe* plant was discovered and selected by the Inventor as a single flowering plant from within the progeny of the stated cross-pollination in a controlled greenhouse environment in De Lier, The Netherlands in 2016.

Asexual reproduction of the new *Kalanchoe* plant by vegetative terminal cuttings in a controlled greenhouse environment in De Lier, The Netherlands since 2016 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalvola'. These characteristics in combination distinguish 'Dokalvola' as a new and distinct *Kalanchoe* plant:

1. Compact, upright and uniformly mounded plant habit.
2. Moderately vigorous growth habit and rapid growth rate.
3. Freely branching plant habit.
4. Dark green-colored leaves.
5. Uniform, early and freely flowering habit.
6. Large single-type flowers that are vivid yellow in color.
7. Excellent postproduction longevity.
8. Relatively tolerant to high temperatures.

Plants of the new *Kalanchoe* can be compared to plants of the female parent selection. Plants of the new *Kalanchoe* differ primarily from plants of the female parent selection in flower petal color as flower petals of plants of the new *Kalanchoe* are darker yellow in color than flower petals of plants of the female parent selection.

Plants of the new *Kalanchoe* can be compared to plants of the male parent selection. Plants of the new *Kalanchoe* differ primarily from plants of the male parent selection in flower type as flowers of plants of the new *Kalanchoe* are single-types whereas flowers of plants of the male parent selection are double-types.

Plants of the new *Kalanchoe* can be compared to plants of the *Kalanchoe blossfeldiana* 'Dokalwilis', disclosed in U.S. Plant Pat. No. 32,482. In side-by-side comparisons, plants of the new *Kalanchoe* differ primarily from plants of 'Dokalwilis' in the following characteristics:

1. Plants of the new *Kalanchoe* are more freely branching than plants of 'Dokalwilis'.
2. Plants of the new *Kalanchoe* are more freely flowering than plants of 'Dokalwilis'.
3. Flower petals of plants of the new *Kalanchoe* are vivid yellow in color whereas flower petals of plants of 'Dokalwilis' are pure white in color.

BRIEF DESCRIPTION OF THE PHOTOGRAPH

The accompanying colored photograph illustrates the overall appearance of the new *Kalanchoe* plant showing the colors as true as it is reasonably possible to obtain in colored reproductions of this type. Colors in the photograph may differ slightly from the color values cited in the detailed botanical description which accurately describe the colors of the new *Kalanchoe* plant. The photograph is a side perspective view of a typical flowering plant of 'Dokalvola' grown in a container.

DETAILED BOTANICAL DESCRIPTION

The aforementioned photograph and following observations, measurements and values describe plants grown during the autumn in 10.5-cm containers in a glass-covered greenhouse in De Lier, The Netherlands and under cultural practices typical of commercial *Kalanchoe* production. During the production of the plants, day temperatures ranged from 20° C. to 25° C., night temperatures ranged from 20° C. to 21° C. and light levels ranged from 10,000 lux to 55,000 lux. Plants received long day/short night conditions (more than 14 hours of light) for four weeks then plants received photoinductive short day/long night conditions (minimum 14 hours darkness) until flowering. Plants were 15 weeks old when the photograph was taken and 19 weeks old when the detailed description was taken. In the detailed description, color references are made to The Royal Horticultural Society Colour Chart, Fifth Edition, except where general terms of ordinary dictionary significance are used.

Botanical classification: *Kalanchoe blossfeldiana* 'Dokalvola'.

Parentage:

*Female, or seed, parent*.—Proprietary selection of *Kalanchoe blossfeldiana* identified as code number KA15-000584-001, not patented.

*Male or pollen parent*.—Proprietary selection of *Kalanchoe blossfeldiana* identified as code number KA15-000623-001, not patented.

Propagation:

*Type*.—By vegetative terminal cuttings.

*Time to initiate roots, summer*.—About 18 days at temperatures about 22° C. to 30° C.

*Time to initiate roots, winter*.—About 21 days at temperatures about 20° C. to 22° C.

*Time to produce a rooted young plant, summer*.—About 22 to 25 days at temperatures about 22° C. to 30° C.

*Time to produce a rooted young plant, winter*.—About 25 to 28 days at temperatures about 20° C. to 22° C.

*Root description*.—Medium in thickness, fibrous; typically greyish white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright and uniformly mounded plant habit; freely flowering habit with numerous cymes positioned above the foliar plane; triangular in shape with rounded crown; appropriate for 10.5-cm containers; moderately vigorous growth habit and rapid growth rate.

*Plant height at flowering*.—About 14 cm.

*Plant diameter at flowering*.—About 20 cm.

*Branching habit*.—Freely branching habit with about 12 to 14 lateral branches developing per plant; pinching (removal of the terminal apex) is not required but will enhance lateral branch development.

Lateral branch description:

*Length*.—About 6 cm to 9 cm.

*Diameter*.—About 2 mm to 4 mm.

*Internode length*.—About 8 mm to 13 mm.

*Aspect*.—Mostly upright.

*Strength*.—Strong.

*Texture and luster*.—Smooth, glabrous; glossy.

*Color, developing and developed*.—Close to 146B.

Leaf description:

*Arrangement*.—Opposite, simple; generally symmetrical.

*Length*.—About 9 cm.

*Width*.—About 6 cm.

*Shape*.—Ovate to elliptical.

*Apex*.—Obtuse.

*Base*.—Obtuse.

*Margin*.—Crenate.

*Texture and luster, upper and lower surfaces*.—Smooth, glabrous; coriaceous; succulent; glossy.

*Venation pattern*.—Pinnate.

*Color*.—Developing leaves, upper surface: Close to 138A. Developing leaves, lower surface: Close to 138B. Fully developed leaves, upper and lower surfaces: Close to N137A; venation, close to 191A.

*Petioles*.—Length: About 1 cm. Diameter: About 7.5 mm to 8.5 mm. Strength: Moderately strong. Texture and luster, upper and lower surfaces: Smooth, glabrous; coriaceous; succulent; glossy. Color, upper surface: Close to 143A. Color, lower surface: Close to 143B.

Flower description:

*Flower arrangement and habit*.—Single-type flowers arranged in axillary cymes; uniform and freely flowering habit with usually more than 500 flower buds and open flowers developing per plant; plants flower continuously for at least eight weeks; flowers face mostly upright to outwardly depending on the position in the inflorescence.

*Fragrance*.—None detected.

*Natural flowering season*.—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Early flowering habit, under short day/long night photoinductive conditions, plants begin flowering about 8.5 to 9.5 weeks; actual time to flower is primarily dependent upon temperature and light intensity.

*Post-production longevity*.—Excellent post-production longevity; plants maintain good foliage and flower maintain good substance for at least three weeks under interior conditions; flowers persistent.

*Flower diameter*.—About 1.8 cm.

*Flower length* (*height*).—About 1.2 cm.

*Flower buds*.—Length: About 1.3 cm. Diameter: About 2.7 mm. Shape: Oblong, becoming tubular/ovoid with development. Texture and luster: Smooth, glabrous; glossy. Color: Close to 14C.

*Petals*.—Quantity and arrangement: Four in a single whorl. Length: About 8 mm. Width: About 8 mm. Shape: Roughly spatulate, rounded. Apex: Acute. Base: Obtuse. Margin: Entire; not undulate. Texture and luster, upper and lower surfaces: Smooth, glabrous; semi-glossy. Color: When opening and fully opened, upper surface: Close to 14A; venation, close to 14A; color does not change with subsequent development. When opening and fully opened, lower surface: Close to 14C; venation, close to 14C; color becoming closer to 22D with subsequent development.

*Sepals*.—Quantity and arrangement: Four in a single whorl. Length: About 6.5 mm. Width: About 2 mm. Shape: Oblong, pointed. Apex: Acute. Base: Obtuse. Margin: Entire. Aspect: Upright. Texture and luster, upper and lower surfaces: Smooth; glabrous; glossy. Color: Developing, upper and lower surfaces: Close to 144B. Fully developed, upper and lower surfaces: Close to 144B.

*Peduncles*.—Length: About 2.5 mm to 3.5 mm. Diameter: About 1 mm. Aspect: Erect, rigid. Strength: Strong. Texture and luster: Smooth, glabrous; glossy. Color: Close to 147B.

*Reproductive organs*.—Androecium: Stamen number: About eight per flower. Anther size: About 0.1 mm by 0.3 mm. Anther shape: Elliptic, flat. Anther color: Close to 165B. Amount of pollen: Moderate. Pollen color: Close to 163B. Gynoecium: Pistil number: About four. Pistil length: About 9.5 mm. Style length: About 7.2 mm. Style color: Close to 138D. Stigma shape: Flat. Stigma color: Close to 8D, crystalline. Ovary color: Close to 138D.

*Seeds, if present*.—Length: About 0.1 mm. Diameter: About 0.05 mm. Texture: Rough. Color: Close to 166C.

Temperature tolerance: Plants of the new *Kalanchoe* have been observed to tolerate temperatures from about 16° C. to about 35° C.

Pathogen & pest tolerance: To date, plants of the new *Kalanchoe* have not been observed to be tolerant to pathogens and pests common to *Kalanchoe* plants.

It is claimed:

1. A new and distinct *Kalanchoe* plant named 'Dokalvola' as herein illustrated and described.

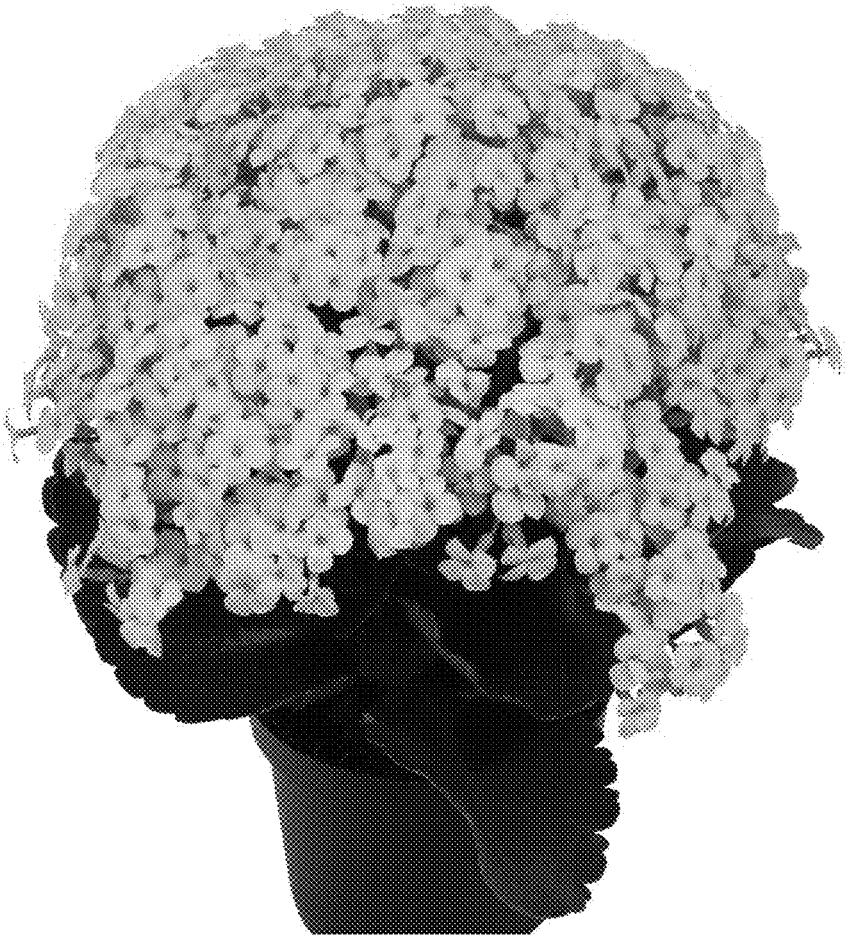

* * * * *